US009278006B2

(12) United States Patent
 Hintermann

(10) Patent No.: US 9,278,006 B2
(45) Date of Patent: Mar. 8, 2016

(54) ANKLE PROSTHESIS WITH NEUTRAL POSITION ADJUSTMENT

(75) Inventor: Beat Hintermann, Liestal (CH)

(73) Assignee: European Foot Platform SC, Saint Louis (FR)

( * ) Notice: Subject to any disclaimer, the term of this patent is extended or adjusted under 35 U.S.C. 154(b) by 751 days.

(21) Appl. No.: 11/553,252

(22) Filed: Oct. 26, 2006

(65) Prior Publication Data

US 2008/0103603 A1 May 1, 2008

(51) Int. Cl.
*A61F 2/42* (2006.01)
*A61F 2/30* (2006.01)
*A61F 2/46* (2006.01)

(52) U.S. Cl.
CPC ............. *A61F 2/4202* (2013.01); *A61F 2/4684* (2013.01); *A61F 2/4657* (2013.01); *A61F 2002/3054* (2013.01); *A61F 2002/30329* (2013.01); *A61F 2002/30387* (2013.01); *A61F 2002/30392* (2013.01); *A61F 2002/30393* (2013.01); *A61F 2002/30398* (2013.01); *A61F 2002/30401* (2013.01); *A61F 2002/30433* (2013.01); *A61F 2002/30518* (2013.01); *A61F 2002/30537* (2013.01); *A61F 2002/30538* (2013.01); *A61F 2002/30542* (2013.01); *A61F 2002/4205* (2013.01); *A61F 2002/4207* (2013.01); *A61F 2002/4658* (2013.01); *A61F 2220/0025* (2013.01)

(58) Field of Classification Search
USPC ....................... 623/20.32, 21.18, 17.14–17.16, 623/20.33–20.34, 21.11–21.14, 23.47
See application file for complete search history.

(56) References Cited

U.S. PATENT DOCUMENTS

| 2004/0143332 A1* | 7/2004 | Krueger et al. ............ 623/17.14 |
| 2005/0049711 A1 | 3/2005 | Ball |
| 2005/0288792 A1 | 12/2005 | Landes et al. |

FOREIGN PATENT DOCUMENTS

| DE | 10123124 | * 12/2002 | ................ A61F 2/42 |
| FR | 2220235 | 10/1974 | |
| WO | 9107931 A1 | 6/1991 | |

OTHER PUBLICATIONS

Search Report for French Patent Application No. 0609417; Jul. 10, 2007.

* cited by examiner

*Primary Examiner* — Yashita Sharma
*Assistant Examiner* — Rebecca Preston
(74) *Attorney, Agent, or Firm* — Perkins Coie LLP

(57) ABSTRACT

An ankle prosthesis (1) having a talar implant (2) designed to be implanted in or on the talus (3), a tibial implant (4) designed to be implanted in or on the tibia (5), and an intermediate implant (6) designed to be interposed between the tibial implant and the talar implant. The intermediate implant (6) is designed to be mounted to move relative to the talar implant (2) at a contact interface (7) in order to allow the ankle to move. The ankle prosthesis (1) has configurable coupling means (10) designed to enable the intermediate implant (6) to be arranged relative to the tibial implant (4) in a specific configuration chosen from among a plurality of possible configurations.

18 Claims, 2 Drawing Sheets

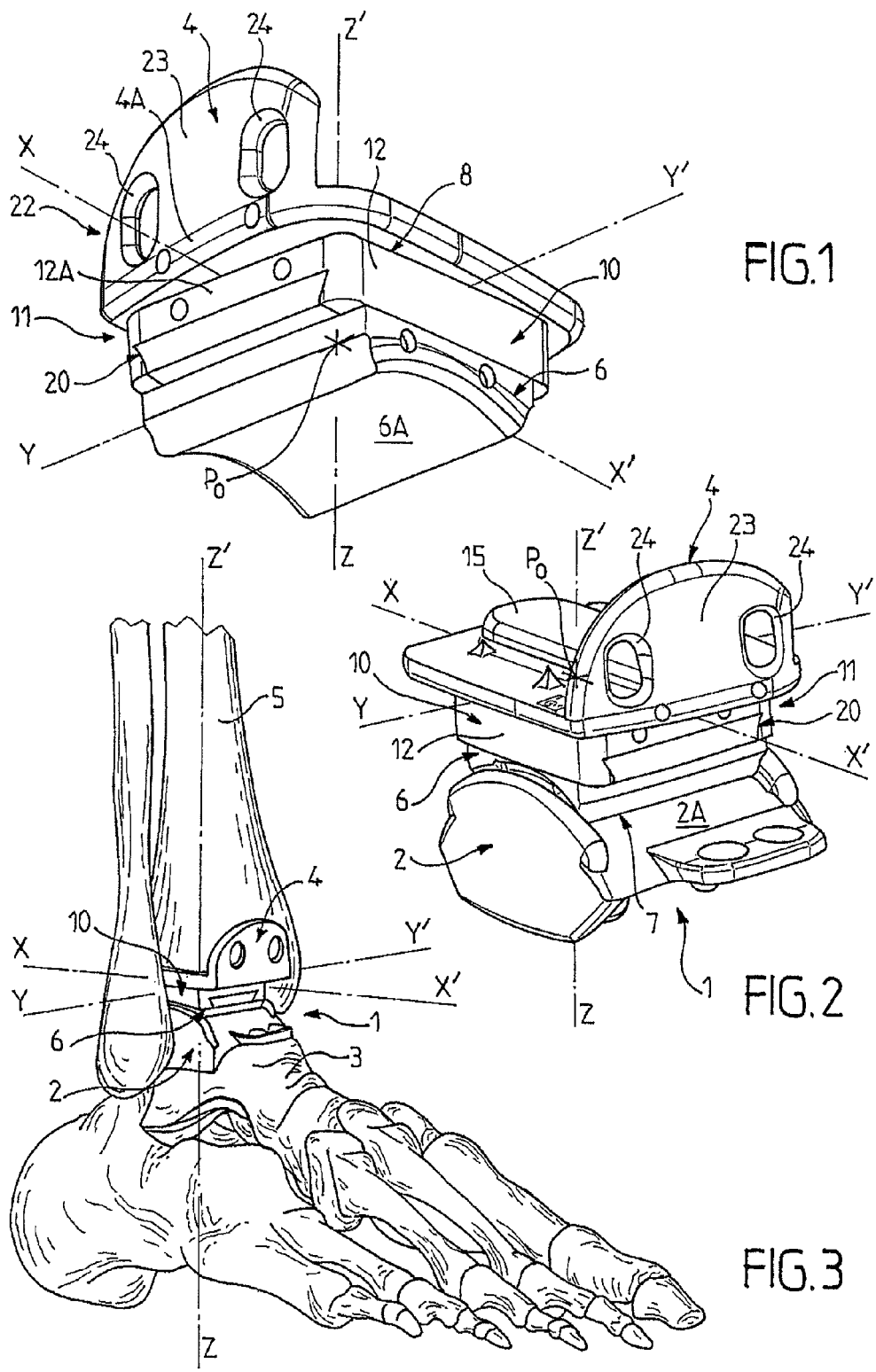

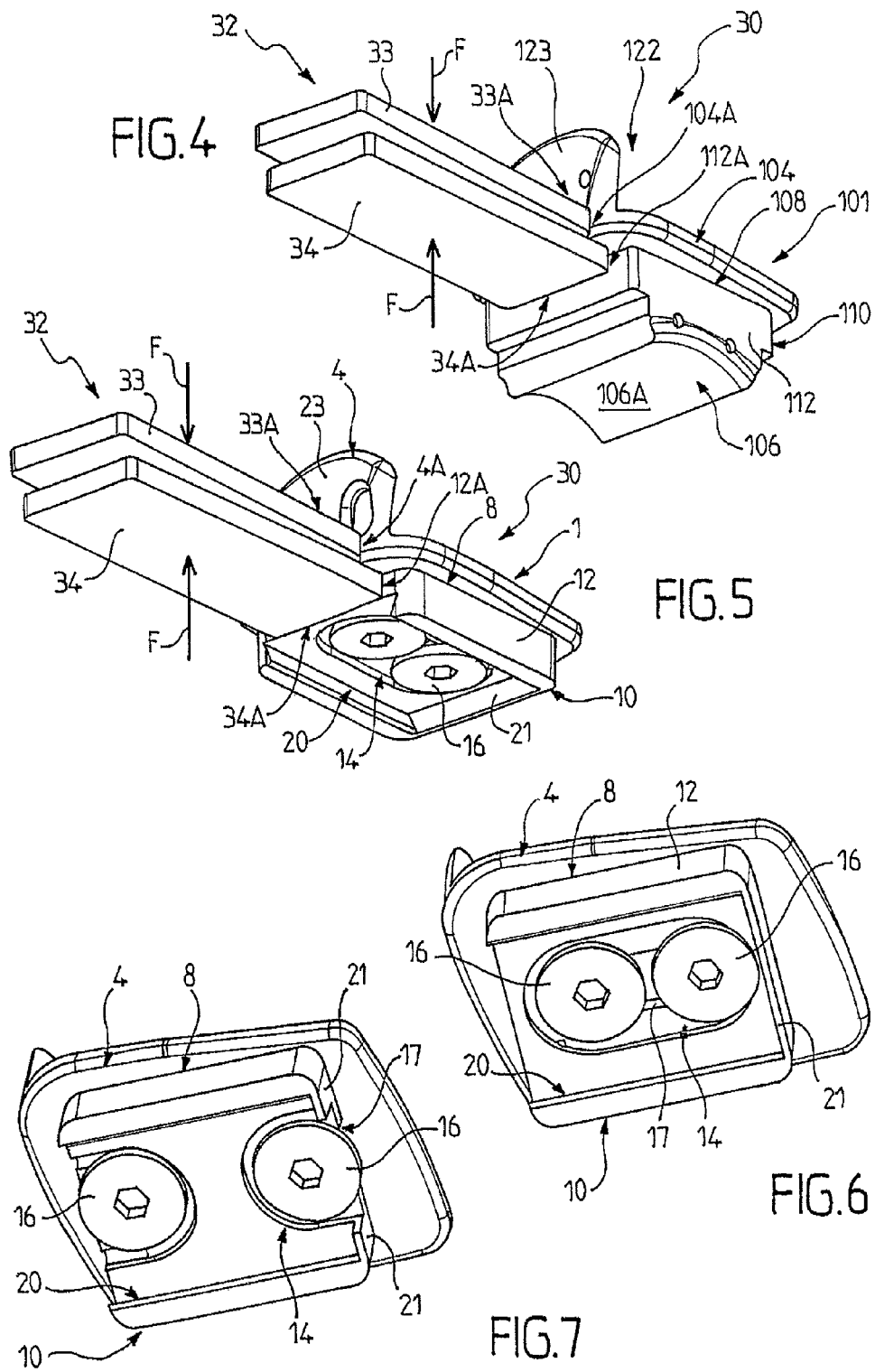

ANKLE PROSTHESIS WITH NEUTRAL POSITION ADJUSTMENT

FIELD OF THE INVENTION

The present invention relates to ankle prostheses designed to orthopedically treat ankle joints; and more particularly, to implants for restoring ankle joint anatomy.

The present invention also relates to a method of preparing an ankle prosthesis as described above.

The present invention also relates to a surgical kit designed for putting an ankle prosthesis into place.

The present invention finally relates to a surgical method of implanting an ankle prosthesis having a talar implant designed to be implanted in or on the talus, a tibial implant designed to be implanted in or on the tibia, and an intermediate implant designed to be interposed between the tibial implant and the talar implant, the intermediate implant being designed to be mounted to move relative to the talar implant at a contact interface in order to allow the ankle to move.

BACKGROUND OF THE INVENTION

It is known that ankle prostheses can be used to restore a certain amount of freedom of movement to the joint of an ankle after the ankle has been damaged totally or partially, e.g., due to impact trauma or to disease.

In particular, it is known that an ankle prosthesis having three implants can be implanted, namely, a talar implant designed to be implanted in or on the talus (anklebone), a tibial implant designed to be implanted in or on the tibia, and an intermediate implant designed to be interposed between the tibial implant and the talar implant.

Generally, the intermediate implant has a large amount of freedom of movement between the other two implants. More particularly, the intermediate implant generally rests in a planar abutment on the tibial implant to allow movement in anteroposterior translation, in mediolateral translation, and in rotation about the medullary axis of the tibia that is substantially perpendicular to the surface of the planar abutment.

Usually, the contact interface between the intermediate implant and the talar implant is a rounded friction surface that is generally cylindrical, spherical, or frustoconical in shape in order to allow the leg to move in plantar flexion and in dorsal flexion relative to the leg.

Although ankle prostheses offer features that are advantageous in terms of movement, the ankle prostheses can be unsuitable for the condition of the patient being treated.

When the patient has already undergone orthopedic treatment limiting the mobility of the ankle, the joint generally suffers from instability due to being weakened by muscle atrophy and/or to tendon laxity. Thus, when, for example, consideration is given to performing arthroplasty (joint replacement) serving to restore joint mobility when the joint has been previously immobilized by arthrodesis (joint fusion), or indeed when it is desired to replace a prosthesis that is an old model and whose movement configuration differs from that of the three-implant prosthesis, suddenly restoring many degrees of freedom that have previously been lost tends to disturb the balance of the patient and exposes the patient to risks of falls, of injuries, and of damage to tissue situated at the joint in question.

Therefore, implementing prior art three-implant prostheses requires patients to undergo a very long period of rehabilitation.

In addition, certain national regulatory requirements prohibit the use of prior art three-implant prostheses.

SUMMARY OF THE INVENTION

A feature of the present invention is a novel ankle prosthesis that does not suffer from the above-mentioned drawbacks and that, while offering satisfactory joint mobility, also guarantees good stability to the ankle joint.

A feature of the present invention is a novel ankle prosthesis that is ergonomic and comfortable during use.

Another feature of the present invention is a novel ankle prosthesis in which wear is minimized and which offers increased longevity.

Another feature of the present invention is a novel ankle prosthesis that is simple and robust in design.

Another feature of the present invention is a novel ankle prosthesis which is easy to implement and, in particular, to implant.

Another feature of the present invention is a novel method of preparing an ankle prosthesis that imparts good stability to the ankle prosthesis.

Another feature of the present invention is a novel method of preparing an ankle prosthesis that makes the prosthesis ergonomic.

Another feature of the present invention is a novel test ankle prosthesis that makes it simpler and more reliable to implement the ankle prosthesis of the present invention.

Another feature of the present invention is a novel test ankle prosthesis that is simple and inexpensive in design.

Another feature of the present invention is a surgical kit for putting an ankle prosthesis into place that, while offering satisfactory joint mobility, also guarantees good stability to the ankle joint, the kit enabling the ankle prosthesis to be implanted simply, accurately, and reliably.

Another feature of the present invention is a novel surgical kit for putting an ankle prosthesis into place that is simple in design and easy to implement.

Another feature of the present invention is a novel surgical method of implanting an ankle prosthesis that makes it possible to impart good stability and satisfactory mobility to the joint.

Another feature of the present invention is a novel surgical method of implanting an ankle prosthesis that optimizes the longevity of the prosthesis and makes the ankle prosthesis more comfortable in use for the patient.

Finally, another feature of the present invention is a novel surgical method of implanting an ankle prosthesis that can be implemented simply, accurately, reliably, and reproducibly.

The present invention provides, in one exemplary embodiment, an ankle prosthesis having a talar implant designed to be implanted in or on the talus, a tibial implant designed to be implanted in or on the tibia, and an intermediate implant designed to be interposed between the tibial implant and the talar implant. The intermediate implant is mounted to move relative to the talar implant at a contact interface in order to allow the ankle to move. The ankle prosthesis has configurable coupling means to enable the intermediate implant to be arranged relative to the tibial implant in a specific configuration chosen from among a plurality of possible configurations.

The features provided by the present invention are also achieved by means of a method of preparing an ankle prosthesis having a talar implant designed to be implanted in or on the talus, a tibial implant designed to be implanted in or on the tibia, and an intermediate implant designed to be interposed between the tibial implant and the talar implant, the intermediate implant further designed to be mounted to move relative to the talar implant at a contact interface in order to allow the ankle to move, the method includes an arrangement step (E1) during which the intermediate implant is arranged relative to the tibial implant, using configurable coupling means with which the prosthesis is provided, in a specific configuration that is chosen, during a selection step (E2), from among a plurality of possible configurations.

The features provided by the present invention are also achieved by means of a test ankle prosthesis designed to be implanted temporarily in place of a final ankle prosthesis that can be configured in a specific configuration chosen from among a plurality of possible configurations, the test ankle prosthesis is arranged so that the test ankle prosthesis can, in vivo, take up any one of the possible configurations, and is provided with reference means arranged to enable the practitioner to take the measurements of the configuration of the test ankle prosthesis so as to reproduce the configuration in the final ankle prosthesis.

The features provided by the present invention are also achieved by means of a surgical kit designed for putting an ankle prosthesis into place, the surgical kit having an ankle prosthesis, referred to as a "final ankle prosthesis," and a test ankle prosthesis, both of which are ankle prostheses of the present invention.

The features provided by the present invention are also achieved by means of a surgical method of putting a "final ankle prosthesis" into place in a patient, the final ankle prosthesis having a talar implant designed to be implanted in or on the talus, a tibial implant designed to be implanted in or on the tibia, and an intermediate implant designed to be interposed between the tibial implant and the talar implant, the intermediate implant further designed to be mounted to move relative to the talar implant at a contact interface in order to allow the ankle to move, the surgical method comprising a step for implanting a test ankle prosthesis, during which step a test ankle prosthesis comprising a test talar implant, a test tibial implant, and a test intermediate implant is implanted in the patient in place of the final ankle prosthesis; a determination step during which a specific configuration of the test ankle prosthesis is determined, in vivo, from among a plurality of possible configurations; and a reproduction step during which the specific configuration chosen during the determination step is reproduced on the final ankle prosthesis by arranging the intermediate implant relative to the tibial implant by configurable coupling means.

The features provided by the present invention are further achieved by means of a surgical method of implanting a "final prosthesis" in a patient, the method comprising an implantation step (K) for implanting a test prosthesis, during the implantation step a test prosthesis that substantially reproduces the shape of the final prosthesis is implanted in the patient in place of the final prosthesis; a determination step (L) during which a particular operating configuration of the test prosthesis is determined, in vivo, from among a plurality of possible configurations; and a reproduction step (M) during which the particular operating configuration chosen during the determination step (L) is reproduced on the final prosthesis by fitting means.

BRIEF DESCRIPTION OF THE DRAWINGS

Other features and advantages of the present invention will appear in more detail on reading the following description and on examining the accompanying drawings, which are given merely by way of non-limiting illustration.

FIG. 1 is a perspective view of a portion of an exemplary embodiment of an ankle prosthesis of the present invention;

FIG. 2 is a perspective view of an ankle prosthesis of the present invention in which the portion shown in FIG. 1 is implemented;

FIG. 3 is a perspective view of the ankle prosthesis of FIG. 2 as implanted in the ankle joint;

FIG. 4 is a perspective view of implementation of a first portion of a surgical kit of the present invention;

FIG. 5 is a perspective view of implementation of a second portion of a surgical kit of the present invention;

FIG. 6 is a perspective view of a second exemplary embodiment of a tibial implant and of coupling means in an ankle prosthesis of the present invention; and FIG. 7 is a perspective view of a third exemplary embodiment of a tibial implant and of coupling means in an ankle prosthesis of the present invention.

DETAILED DESCRIPTION OF THE INVENTION

The ankle prosthesis 1 of the present invention is designed to restore, at least partially, the mobility of an ankle joint in a patient who has, in particular, suffered disease or impact trauma.

The ankle prosthesis 1 of the present invention can also be used to replace a previously implanted ankle prosthesis.

The ankle prosthesis 1 of the present invention comprises a talar implant 2 designed to be implanted in or on the talus (anklebone) 3 and a tibial implant 4 designed to be implanted in or on the tibia 5.

The ankle prosthesis 1 further comprises an intermediate implant 6 which is designed to be interposed between the tibial implant 4 and the talar implant 2.

The intermediate implant 6 is designed to be mounted to move relative to the talar implant 2 at a contact interface 7, in order to allow the ankle to move. The intermediate implant 6 can, in particular, be made of polyethylene.

More precisely, the intermediate implant 6 preferably has a contact surface 6A that is designed to come into abutment against a surface 2A of the talar implant 2 that is of complementary shape, so that the intermediate implant can move by sliding, with friction, relative to the talar implant 2.

Most preferably, the complementary contact surfaces 2A, 6A are rounded in shape, e.g., substantially spherically, cylindrically or frustoconically rounded, so as to allow the foot to move in plantar flexion and in dorsal flexion relative to the leg.

According to an important characteristic of the present invention, the prosthesis 1 is provided with configurable coupling means 10 designed to enable the intermediate implant 6 to be arranged relative to the tibial implant 4 in a specific configuration chosen from among a plurality of possible configurations.

The coupling means 10 make it possible to act on the prosthesis 1 to enable the practitioner to select that arrangement of the intermediate implant 6 relative to the tibial implant 4 which the practitioner deems most appropriate for each specific case and from among a plurality of potential choices.

The coupling means 10 that are configurable in the meaning of the present invention make it possible to improve the stability of the prosthesis 1, and therefore the stability of the ankle joint, by keeping control over the relative mobility of the intermediate implant 6 and of the tibial implant 4, e.g., by setting limits for it.

In accordance with the present invention, it is possible to imagine the coupling means 10 being designed to restrict the amplitude of movement in one or more of the freedoms allowed by the moving connection that the coupling means forms between the intermediate implant 6 and the tibial implant 4. For example, if the intermediate implant 6 is in planar abutment against the tibial implant 4, as in prior art three-implant prostheses, the coupling means 10 of the present invention can include abutments or guide elements that limit the strokes in translation in the contact plane, e.g., in a manner such that the connection cannot be totally dislocated by uncontrolled movement over too large an amplitude.

However, the coupling means 10 are preferably designed to form a moving connection of the interfitting type between the intermediate implant 6 and the tibial implant 4. For this purpose, the configurable coupling means 10 preferably include engagement means 11 for engaging the intermediate implant 6 in the tibial implant 4.

Thus, in a preferred exemplary embodiment shown in particular in FIGS. 1 and 2, the coupling means 10 constitute fastening means designed to secure the intermediate implant 6 to the tibial implant 4.

Insofar as the coupling means 10 of the present invention make it possible to restrain or even to prevent movements of the intermediate implant 6 relative to the tibial implant 4, mechanical stresses appear at the implants when the prosthesis 1 is involved in movements made by the patient, in particular, during walking.

Such stresses can cause premature wear on any one of the components implants 2, 4, 6 of the prosthesis 1, or can generate deformation or even breakage of the implants 2, 4, 6.

That is why the specific configuration is preferably chosen as a function of the particular shape of the patient's joint in which the prosthesis 1 is to be implanted. In other words, it is advantageously possible to adjust the prosthesis 1 of the present invention as a function of the specific anatomy of the patient.

Most preferably, the specific configuration of the intermediate implant 6 relative to the tibial implant 4 is chosen such that the stresses exerted on the intermediate implant 6 and on the tibial implant 4 during the natural movements of the ankle are minimized overall. It is then referred to as the "neutral configuration".

More precisely, it should be noted that, in a healthy person, the ankle joint allows the tibia 5 to move in a plurality of movements relative to the talus 3, and in particular, in addition to the dorsal flexion and plantar flexion movements, namely:

a movement in anteroposterior translation substantially along an axis (XX'), when the leg tends to move "forwards" or "backwards" relative to the foot while the foot remains stationary;

a movement in mediolateral translation along an axis (YY') when the leg tends to move laterally inwards towards the patient's other leg or outwards away therefrom while the foot remains stationary; and a movement in rotation about the medullary axis (ZZ') of the tibia, when the leg tends to pivot through a yaw angle relative to the foot that remains stationary.

The three above-described movements are generally of small amplitude.

As shown in FIG. 3, when the patient is upright in the standing position and when the foot is resting on a flat and horizontal surface, the axis (XX') is substantially horizontal and parallel to the sagittal plane of the patient (i.e., the axis (XX') extends in the direction in which the patient is facing), the axis (YY') is substantially horizontal, extending towards one side of the patient, and substantially orthogonal to the axis (XX'), while the axis (ZZ') extends substantially vertically and forms a normal to the plane defined by the axes (XX') and (YY').

It is known that, for each patient, as a function of his or her own specific anatomy, a point of origin $P_O$ exists about which the movements in anteroposterior translation, in mediolateral translation, and in rotation about the medullary axis (ZZ') of the tibia 5 take place. Geometrically, the point of origin $P_O$ substantially corresponds to the virtual intersection between the axes (XX'), (YY'), and (ZZ').

In addition, when a prosthesis 1 is implanted in the patient, the prosthesis, by construction, defines one or more movement axes which make it possible to restore, at least partially, one or more degrees of freedom for the joint.

The configuration that is neutral in the meaning of the present invention thus corresponds to the intermediate implant 6 being in a position relative to the tibial implant 4 in which the intermediate implant 6 is substantially centered relative to the point of origin $P_O$ and in which the tibial implant 4 and/or the intermediate implant 6 is/are oriented such that the movement axes of the prosthesis 1 substantially coincide with the natural anatomical axes of the ankle of the patient.

By way of example, if the contact zone 8 between the intermediate implant 6 and the tibial implant 4 is arranged so as that the intermediate implant 6 and the tibial implant 4 are in planar abutment, the contact zone 8 should be substantially normal to the axis (ZZ') and located in the immediate vicinity of the translation axes (XX') and (YY'), and preferably superposed on the plane formed by the translation axes.

For purposes of the description below, the expression "neutral configuration" applies to the prosthesis 1 as a whole, or to the coupling means 10, or to any other component element of the prosthesis 1 when the prosthesis is considered in the situation in which the prosthesis finds itself when the arrangement of the intermediate implant 6 relative to the tibial implant 4 corresponds to the neutral configuration.

Particularly advantageously, by offering the possibility of placing the intermediate implant 6 in the neutral configuration, the configurable coupling means 10 of the present invention make it possible to minimize the amplitude of any residual movements of the intermediate implant 6 relative to the tibial implant 4 and/or to limit the stresses exerted on the elements when the implants 4, 6 are secured to each other.

In addition, the possibility of adjustment offered by the coupling means 10 makes it possible to adapt the prosthesis 1 to fit the shape of the joint specific to each patient, thereby enabling the prosthesis 1 to be adjusted finely, accurately, and in personalized manner.

It is thus possible to prevent, to a large extent, discomfort in use and excessive wear that would inevitably result from arbitrary restriction of the intermediate implant 6 on the tibial implant 4 in a single configuration that is pre-determined by construction in the prosthesis itself, and that would not always correspond to the anatomy of the patient in question.

In a preferred exemplary embodiment shown, in particular, in FIGS. 1, 2, 5, 6, and 7, the configurable coupling means 10 include a base 12 designed to be fastened to the tibial implant 4 and to form a mechanical interface between the tibial implant 4 and the intermediate implant 6.

The base 12 is preferably substantially in the shape of a rectangular block.

Preferably, the base 12 is provided with adjustable fastening means 14 which make it possible to choose, from among a plurality of possible positions, the position in which the base 12 is actually fastened relative to the tibial implant 4.

Naturally, the configuration of the contact zone 8 between the tibial implant 4 and the base 12 is not limited to one particular embodiment. However, the contact zone 8 between the tibial implant 4 and the base 12 is preferably substantially plane and, more preferably, the contact zone 8 coincides substantially with the plane defined by the axes (XX') and (YY').

Thus, it is advantageously possible to press the base 12 against the tibial implant 4 and to position the base 12 relative thereto in a wide variety of positions and of orientations, by using the degrees of freedom offered by the resulting free planar abutment connection. Final fastening, for locking the base 12 firmly, can take place after the neutral configuration has been identified.

In a preferred exemplary embodiment, the adjustable fastening means 14 enable the position in which the base 12 is fastened relative to the tibial implant 4 to be adjusted continuously, e.g., by means of a screw cooperating with an oblong hole or by means of any other suitable mechanism.

In particular, as shown in FIGS. 5-7, the adjustable fastening means 14 can comprise a plurality of broad-headed screws 16 cooperating with one or more grooves 17 provided in the base 12 and dimensioned such that the residual clearance between the shanks of the screws 16 and the edges of the grooves 17 makes it possible to adjust the position of the base 12 linearly and/or angularly relative to the tibial implant 4. Thus, it is possible to couple the base 12 loosely to the tibial implant 4, and then to adjust the position, and finally to tighten the screws 16 in order to press the base 12 and to hold the base 12 stationary against the tibial implant 4. A projection 15, as shown in FIG. 2, can also be provided on the tibial implant 4 firstly to provide a reference element enabling the tibial implant 4 to be positioned mediolaterally in a reproducible manner relative to the tibia 5, and secondly to impart to the tibial implant 4 the thickness of material that is required by the use of the screws 16.

In a preferred alternative exemplary embodiment, the base 12 is provided with reception means 20 making it possible to connect the intermediate implant 6 to the base 12.

Most preferably, the reception means 20 are arranged so that the intermediate implant 6 can occupy only a single and predetermined position relative to the base 12.

Various solutions can be devised for implementing the reception means 20, and in particular, tongue-and-groove systems or systems having screws, the systems preferably associated with keying means such as centering studs, notches, or lugs.

In a preferred alternative exemplary embodiment, shown, in particular, in FIGS. 1, 2, and 5, the reception means 20 are formed by a dovetail making it possible for the intermediate implant 6 to be inserted by being slid laterally into the base 12.

In this alternative exemplary embodiment, it suffices to lock the intermediate implant in translation along the generator axis of the dovetail in order to obtain an interfitting connection between the base 12 and the intermediate implant 6.

Preferably, an abutment element 21 is provided against which the intermediate implant 6 comes into abutment when inserted fully into the base 12, and non-return means (not shown) are provided that oppose extraction of the intermediate implant 6 from the base 12 after the intermediate implant has been inserted into the base.

In a manner well known to a person skilled in the art, such non-return means can, for example, be formed by snap-fastening, in particular, by means of a moving lip projecting from one of the faces of the intermediate implant 6 that come into contact with the base 12, the lip deforming elastically or retracting while the intermediate implant 6 is inserted into the base 12 and then re-deploying into a notch provided for that purpose in the base once the intermediate implant has reached the abutment position.

Thus, according to the present invention, the engagement means 11 for engaging the intermediate implant 6 into the tibial implant 4 can advantageously be formed by the combination of the base 12, of the adjustable fastening means 14 and of the reception means 20.

Once in position in the dovetail, the intermediate implant 6 can advantageously serve to lock the heads of the fastening screws 16, thereby preventing any untimely appearance of slack between the base 12 and the tibial implant 4 due to the screws 16 coming loose accidentally.

In a preferred alternative exemplary embodiment, the ankle prosthesis 1 further comprises reference means 22 designed to indicate how the intermediate implant 6 is arranged relative to the tibial implant 4 in order to enable the practitioner to configure the configurable coupling means 10 accurately. In other words, the reference means 22 inform the practitioner of the configuration in which the configurable coupling means 10, and more generally the prosthesis 1, find themselves.

More particularly, the reference means 22 of the present invention can constitute three-dimensional reference means designed to inform the practitioner of how the intermediate implant 6 and/or the base 12 is/are disposed relative to the tibial implant 4.

Thus, it is advantageously possible to know, and therefore, as described in detail below, to reproduce, the arrangement of the prosthesis 1 that corresponds to a particular configuration, in particular the neutral configuration.

Preferably, the reference means 22 comprise a first reference surface 4A associated with the tibial implant 4 and a second reference surface 12A associated with the base 12, the relative position of the first and second reference surfaces 4A, 12A making it possible to determine and, more generally, to indicate, both visually and physically, the position of the base 12 in the frame of reference formed by the tibial implant 4.

In a preferred alternative exemplary embodiment, the tibial implant 4 has a tongue 23 that forms both a tibial shield preventing excessive development of bone cells that could hinder operation of the joint, and also a fastening tab provided with oblong holes 24 that serve to receive screws for fastening to the bone. The first reference surface 4A can then advantageously be formed by a sector of the anterior face of the tongue 23 that is preferably substantially plane.

In an analogous manner, the second reference surface 12A is preferably formed by a substantially plane face of the base 12.

Advantageously, as described in detail below, the first and second reference surfaces 4A, 12A make it possible to adjust the position of the base 12 accurately relative to the tibial implant 4 during assembly of the prosthesis 1.

The present invention also relates to a method of preparing an ankle prosthesis 1 comprising a talar implant 2 designed to be implanted in or on the talus 3, a tibial implant 4 designed to be implanted in or on the tibia 5, and an intermediate implant 6 designed to be interposed between the tibial implant 4 and the talar implant 2, the intermediate implant 6 further designed to be mounted to move relative to the talar implant 2 at a contact interface 7, in order to allow the ankle to move, the method includes an arrangement step (E1) during which the intermediate implant 6 is arranged relative to the tibial implant 4, using configurable coupling means 10 with which the prosthesis 1 is provided, in a specific configuration that is chosen, during a selection step (E2), from among a plurality of possible configurations.

Preferably, during the selection step (E2), the specific configuration is chosen as a function of the particular shape of the patient's joint in which the prosthesis 1 is to be implanted, and, more preferably, the neutral configuration that is specific to the patient is chosen as the specific configuration.

In a first alternative exemplary embodiment of the method, the preparation method can advantageously be implemented in the factory, as an assembly step of a method of manufacturing a made-to-measure ankle prosthesis to be delivered pre-assembled in the neutral configuration.

It is possible, in particular, to imagine that a hospital practitioner can, after having performed a diagnostic and having taken biometric measurements on the patient, e.g., by medical imaging, remotely order a prosthesis 1 from the manufacturer for a future operation merely by transmitting to the manufacturer the dimensional specifications including the key data relating to assembly of the component elements of the prosthesis, and by leaving the manufacturer to perform the appropriate assembly and packaging of the prosthesis.

In another exemplary embodiment, the preparation method can be implemented during a surgical operation by the surgeon, during which the surgeon personally configures the prosthesis 1 at the time of implantation.

The present invention also relates to a test ankle prosthesis 101 designed to be implanted temporarily in place of a final ankle prosthesis that can be configured in a specific configuration chosen from among a plurality of possible configurations, the test ankle prosthesis firstly arranged so that the test ankle prosthesis can, in vivo, take up any one of the possible configurations, and secondly provided with reference means 122 arranged to enable the practitioner to take the measurements of the configuration to reproduce the configuration in the final ankle prosthesis.

For purposes of the present invention, the test ankle prosthesis 101 and the final ankle prosthesis are preferably designed to be used during a single surgical operation, the test ankle prosthesis firstly being put into place in the ankle joint in order to enable the neutral configuration that is specific to the patient to be identified and referenced, and then being removed and replaced with the final ankle prosthesis 1 whose intermediate implant 6 is positioned and fastened to the tibial implant 4 as a function of the result of the three-dimensional referencing of the neutral configuration that is performed on the test ankle prosthesis 101.

In other words, the test ankle prosthesis 101 preferably constitutes an intermediate implantation accessory that makes it possible, in the patient, to take the topographical measurements necessary for the final ankle prosthesis to be in the correct configuration, and the test ankle prosthesis is not an operational prosthesis designed to remain durably in the joint and to withstand stresses related to walking.

Advantageously, the test ankle prosthesis 101 can present a structure that is simplified compared with the final ankle prosthesis, and in particular, that can be implemented using materials that are less strong and less expensive than the materials used for the final ankle prosthesis.

Preferably, the final ankle prosthesis is formed by an ankle prosthesis 1 as described above, and the test ankle prosthesis 101 comprises a test talar implant 102, a test tibial implant 104, a test intermediate implant 106 and test configurable coupling means 110 whose shapes and dimensions correspond substantially to the shapes and dimensions respectively of the talar implant 2, of the tibial implant 4, of the intermediate implant 6, and of the configurable coupling means 10.

By numbering convention, the references given to the component elements of the test ankle prosthesis 101 correspond to the references of the analogous component elements of the final ankle prosthesis plus 100.

In a preferred alternative exemplary embodiment, the test intermediate implant 106 and the test configurable coupling means 110, and more precisely the test base 112 thereof, form a one-piece unit of the block type 106, 110, as shown in FIG. 4.

In accordance with the present invention, it is not absolutely necessary to reproduce the configurable coupling means 10 exactly on the test ankle prosthesis 101.

If it is decided to opt for an alternative exemplary embodiment of the final ankle prosthesis 1 in which the intermediate implant 6 can take up only one position relative to the base 12, firstly it is necessary and sufficient, in order to define the neutral configuration completely, to know merely the position of one or the other of the two elements relative to the tibial implant 4.

Secondly, insofar as only the mobility of the test intermediate implant 106 relative to the test tibial implant 104 is then of interest in seeking the appropriate position to be imparted to the base 12, it is not essential to provide the equivalent of the fastening means 14 on the test ankle prosthesis 101.

It is thus advantageously possible, in the test ankle prosthesis 101, to model the unit formed by the base 12 and by the intermediate implant 6, which can be likened dynamically to a single solid, by a block 106, 110 reproducing merely the outside working dimensions and shapes of the unit.

In a particularly preferred alternative exemplary embodiment, the surface of the block 106, 110 which is designed to come into contact with the test tibial implant 104, at the contact zone 108, is substantially plane, smooth, and without any fastening means.

Naturally, other simplifications of the component elements of the test ankle prosthesis 101 can be made relative to their counterparts in the final ankle prosthesis 1 without going beyond the ambit of the present invention, providing that the simplifications are not detrimental to the feasibility and to the validity of determining the neutral position.

Such simplifications, associated with the use of inexpensive materials, advantageously make it less expensive to produce a test ankle that is suitable for being sterilized and used a plurality of times.

In addition, the test ankle prosthesis 101 of the present invention can advantageously be provided with self-centering means arranged to bring the test ankle prosthesis into a neutral configuration, in which the stresses exerted on the test intermediate implant 106 and on the test tibial implant 104 during natural movements of the ankle are minimized. In other words, the self-centering means spontaneously tend to place the test ankle prosthesis 101 in a neutral configuration, preferably under the effect of natural movements that the surgeon imparts to the foot of the patient relative to the leg of the patient.

To this end, the self-centering means are preferably formed by the block 106, 110, which is then arranged to be interposed freely between the test talar implant 102 and the test tibial implant 104 firstly in plane abutment connection therewith, at the contact interface 8, and more particularly in the plane defined by the axes (XX') and (YY'), and secondly in preferably sliding pivotal connection with the test talar implant 102, at the rounded surface 106A.

Such an arrangement imparts self-centering behavior to the block 106, 110 due to the fact that, when the test ankle prosthesis 101 is implanted and when the block 106, 110 is positioned between the test tibial implant 104 and the test talar implant 102, in contact with the implants via opposite ones of the faces, the surgeon, by manipulating the foot relative to the leg, can, under the effect of the dynamic stresses generated in the joint, cause the block 106, 110 to be moved progressively through the degrees of freedom allowed by the plane abutment, until the block reaches a position that is substantially centered on the position of origin $P_O$ in which the state of the dynamic stresses is minimized.

Preferably, the reference means 122 are arranged to cooperate with the touch-sensitive members 33, 34 of measurement means 32 designed to enable the practitioner to take the measurements of the configuration of the test ankle prosthesis 101 when the ankle prosthesis is implanted in the patient.

Most preferably, the reference means 122 are secured to the touch-sensitive members 33, 34 prior to implantation of the test ankle prosthesis, and cooperate with the test ankle prosthesis while the test ankle prosthesis is implanted. Thus, it is possible, in particular, to obtain continuous monitoring of changes in the configuration of the test ankle prosthesis in vivo.

To this end, the dimensional and functional mimicry existing between the test ankle prosthesis 101 and the final ankle prosthesis 1 advantageously enables the practitioner to take the position measurements directly on the test ankle prosthesis 101, the distances and the orientations of the component elements of the test ankle prosthesis faithfully expressing the configuration that should be reproduced with the final ankle prosthesis 1.

The present invention also relates to a surgical kit 30 that is designed for putting an ankle prosthesis into place.

According to the present invention, the surgical kit 30 comprises the ankle prosthesis 1 of the present invention, referred to as a "final ankle prosthesis," and a test ankle prosthesis 101 as described above.

Preferably, the surgical kit 30 of the present invention further comprises measurement means 32 designed to enable the practitioner to take the measurements of the configuration of the test ankle prosthesis 101 while the test ankle prosthesis 101 is implanted in the patient.

More precisely, the measurement means 32 are preferably designed to take the measurements of the position of the test coupling means 110, or of the block 106, 110, relative to the test tibial implant 104, in particular when the test ankle prosthesis 101 is in the neutral configuration so that the stresses exerted on the intermediate implant 106 and on the tibial implant 104 during the natural movements of the ankle are minimized.

The measurement means 32 of the present invention can use either contact measurement technology of the feeler type or remote measurement technology of the laser beam type. It is also possible to use explicit measurement, e.g., by enabling the practitioner to quantify a linear offset (in millimeters) and/or an angular offset (in degrees) of the block 106, 110 relative to the tibial implant 104, or preferably, to use an implicit measurement of the neutral configuration by shaping a template that gives the relative position of these elements.

Preferably, the measurement means 32 comprise a first touch-sensitive member 33 presenting a first feeler surface 33A and a second touch-sensitive member 34 presenting a second feeler surface 34A, the feeler surfaces being designed to come into contact respectively with the test tibial implant 104 and with the test intermediate implant 106.

More precisely, as shown in FIG. 4, the second feeler surface 34A is preferably arranged to come into contact with the test base 112 that forms the bottom of the block 110.

In a preferred alternative exemplary embodiment, the first and second touch-sensitive members 33, 34 are provided with association means for associating them respectively with the test tibial implant 104 and with the test intermediate implant 106 so that it is possible firstly for them to be secured to the respective ones of these implants prior to implantation of the test ankle prosthesis 101 and secondly for them to remain secured to the implants while the test ankle prosthesis 101 is inside the patient.

In particular, for this purpose, it is possible to use a system of pegs that project from the feeler surfaces and designed to fit into holes provided in first and second test reference surfaces 104A, 112A associated respectively with the test tibial implant 104 and with the base 112 of the block 106, 110.

Thus, the measurement means 32 of the present invention are suitable for continuously evaluating the configuration of the implanted test ankle prosthesis 101 by monitoring, in real time, the movements of the test intermediate implant 106 relative to the test tibial implant 104.

Preferably, the association means are arranged to enable each of the touch-sensitive members 33, 34 to be aligned with and fastened to the test reference surface 104A, 112A that is associated with the touch-sensitive members 33, 34 in a single and reproducible position.

Preferably, the first and second touch-sensitive members are formed respectively by first and second extension leaves, each of which has one end that, when the test ankle prosthesis 101 is implanted, projects from the incision made to access the ankle of the patient.

Most preferably, as shown in FIGS. 4 and 5, each of the first and second touch-sensitive member 33, 34 is formed of a rectangular plate, the two plates advantageously being associated with each other to form a free plane abutment connection that is co-planar with the contact zone 8, 108, i.e., that is co-planar with the plane formed by the axes (XX') and (YY') when the test ankle prosthesis 101 is implanted.

Preferably, the first and second touch-sensitive members 33, 34 are coupled together by reversible or releasable locking means so that the first and second touch-sensitive members 33, 34 can be allowed to move relative to each other or else be constrained to move with each other.

In a particularly preferable alternative exemplary embodiment shown in FIGS. 4 and 5, the two touch-sensitive members 33, 34 can be constrained to move with each other simply and reliably by means of vise-grip pliers (not shown) that tend to compress them one against the other, at the portion that projects beyond the incision, by exerting a clamping force F that is substantially normal to the contact plane 108.

Thus, implementing the reversible locking means does not disturb the positions of the first and second touch-sensitive members 33, 34 or of the test tibial implant 104, or of the block 106, 110 once the neutral configuration is reached by the test ankle prosthesis 101.

Preferably, the first and second test reference surfaces 104, 112 are substantially identical respectively to the first and second reference surfaces 4, 12 of the final ankle prosthesis 1 so that the first and second touch-sensitive members 33, 34 can engage similarly and equally well the final tibial implant 4 and the test tibial implant 104, or the final base 12 and the test base 12.

In addition, the final ankle prosthesis 1 preferably has elements complementary to the association means for association with the test tibial implant 104 and with the test intermediate implant 106, in particular, holes designed to receive the pegs on the touch-sensitive members 33, 34.

Thus, the test ankle prosthesis 101 and the final ankle prosthesis 1 are interchangeable so that, after referencing the neutral configuration on the test ankle prosthesis, after fastening the touch-sensitive members 33, 34 together, and after disengaging the touch-sensitive members from the test ankle prosthesis 101, it is possible to place the tibial implant 4 and the base 12 so that the tibial implant 4 and the base 12 are respectively touching the first and second feeler surfaces 33A, 34A, and to position these elements in the neutral configuration.

In other words, the measurement means 32 of the present invention are preferably also designed to enable the configuration of the test ankle prosthesis 101 to be transposed to the final ankle prosthesis 1, the measurement means 32 forming an assembly template for the final ankle prosthesis 1.

Such a preferred alternative exemplary embodiment of the measurement means 32 makes it possible for the configuration to be transposed rapidly, simply, and accurately, the measurement taken on the test ankle prosthesis 101 and the reproduction on the final ankle prosthesis 1 taking place immediately and intuitively without it being necessary for the practitioner to seek to know explicitly any intermediate value, such as a linear or angular offset.

Naturally, the present invention can concern the measurement means 32 considered separately in their own right, and more precisely an adjustable template making it possible to take the physical measurements of a particular configuration by the test ankle prosthesis 101 and to transpose the configuration onto the final ankle prosthesis 1.

In accordance with the present invention, the final ankle prosthesis 1 can advantageously be assembled outside the operating drape, on an accessory workstation, under conditions that are particularly easy and practical, in particular in terms of accessibility, lighting, cleanness, etc.

Furthermore, in an alternative exemplary embodiment of the kit 30 of the present invention, the final talar implant 2 also serves as the test implant 102, and, by being put into place directly, the final talar implant 2 advantageously limits the trauma suffered by the talus by sparing the talus the replacement of one implant with another implant. For reasons of clarity, reference is made in the present description to a "test talar implant 102" in order to designate the final talar implant 2 when the final talar implant 2 is used as an element of the test ankle prosthesis 101 for evaluating the configuration in which the final ankle prosthesis 1 is to be implanted.

By giving the test tibial implant 104 mediolateral and anteroposterior centering structures that are homologous to the those of the final tibial implant 4, namely respectively a projection (not shown) and a tibial shield 123, it is possible to position the final tibial implant 4 relative to the tibia 5 immediately in a position identical to the position previously occupied by the test tibial implant 104.

Naturally, the surgical kit of the present invention is not limited to implanting an ankle prosthesis and can be supplied in other forms for implementing other prostheses, in particular, joint prostheses. A person skilled in the art can naturally determine the appropriate dimensioning and shapes for the component elements of the final prosthesis and of the test prosthesis resulting from such an adaptation.

The present invention also relates to a surgical method of putting a "final ankle prosthesis" into place in a patient, the final ankle prosthesis 1 comprising a talar implant 2 designed to be implanted in or on the talus, a tibial implant 4 designed to be implanted in or on the tibia 4, and an intermediate implant 6 designed to be interposed between the tibial implant and the talar implant, the intermediate implant 6 further designed to be mounted to move relative to the talar implant 2 at a contact interface 7 in order to allow the ankle to move.

Most preferably, the method can be implemented using a surgical kit 30 as described above, to which reference is made by way of a particular example.

According to the present invention, the surgical method includes a step (a) for implanting a test ankle prosthesis, during which step a test ankle prosthesis 101 comprising a test talar implant 102, a test tibial implant, and a test intermediate implant 106 is implanted in the patient in place of the final ankle prosthesis.

More precisely, after preparing the bone surfaces in question, in particular by resection, the practitioner mounts and temporarily fastens the test talar implant 102 in or on the talus 3 and the test tibial implant 104 in or on the tibia 5. The practitioner then roughly positions the block 106, 110 in the joint, by interposing the block between the test tibial implant 104 and the test talar implant 102, so that firstly the surface 106A of the block comes into contact with the surface 102A of the test talar implant so that it can slide thereon with friction, and secondly so that the opposite surface comes into free plane abutment against the test tibial implant 104 at the contact zone 108.

The surgical method of the present invention also includes a determination step (b) during which a specific configuration of the test ankle prosthesis is determined in vivo from among a plurality of possible configurations.

Preferably, during the determination step (b), a "neutral configuration" is identified empirically as the specific configuration of the test ankle prosthesis 101, in which neutral configuration the stresses exerted on the test ankle prosthesis 101 during natural movements of the ankle joint are minimized.

Most preferably, the determination step (b) for determining the specific configuration comprises a patient manipulation sub-step (b1) during which the patient is placed in a predetermined posture to observe the behavior of the test ankle prosthesis 101 under the effect of the manipulation, and an adjustment sub-step (b2) during which the configuration of the test ankle prosthesis 101 is modified as a function of the behavior observed during the sub-step (b1).

More particularly, the practitioner can force the foot to move relative to the leg, in particular by causing the foot to undergo plantar flexion followed by dorsal flexion in order to observe the response from the block 106, 110 to these manipulations.

Preferably, during the determination step (b), a plurality of manipulation sub-steps (b1) are performed successively, each of which is followed by an adjustment sub-step (b2) so as to adjust the configuration of the test ankle prosthesis 101 iteratively. The practitioner can, in particular, put the patient cyclically through a plurality of distinct postures in a determined sequence, and, for example, alternate dorsal flexions and plantar flexions repetitively.

Advantageously, under the effect of the manipulations of the joint, the block 106, 110 tends spontaneously to become centered on the position $P_O$ in which the stresses to which the block 106, 110 is subjected during the movements of the joint are substantially minimized.

In other words, the manipulation sub-step (b1) and the adjustment step (b2) preferably coincide with each other, the test ankle prosthesis 101 is designed to be self-configuring in response to one or more manipulations of the patient.

Thus, the surgeon can, by constraining the block 106, 110 to migrate iteratively by means of successive manipulations of the foot relative to the leg, cause the test ankle prosthesis 101, and more particularly the block 106, 110, to converge progressively towards the neutral configuration.

The surgical method of the present invention further includes a reproduction step (c) during which the specific configuration chosen during the determination step (b) is reproduced on the final ankle prosthesis 1 by arranging the intermediate implant 6 relative to the tibial implant 4 by means of configurable coupling means 10.

Preferably, since the entire method is applied during a single surgical operation, the method includes a replacement step (d) during which the test ankle prosthesis 101 is extracted and the final ankle prosthesis 1 as placed in the chosen specific configuration is implanted in place of the test ankle prosthesis.

To this end, the replacement step (d) can concern all or part of the test ankle prosthesis, it being possible, for example, for the test talar implant 102 to be kept and used as the final talar implant 2.

Preferably, the surgical method includes a preparation step (e) for preparing the test ankle prosthesis 101, during which step, the test ankle prosthesis is associated with measurement means 32 designed to enable the practitioner to take the measurements of the configuration of the test ankle prosthesis 101 while the test ankle prosthesis is implanted in the patient.

The preparation step (e) can advantageously be performed prior to the implantation step (a) for implanting the test ankle prosthesis 101, so that it is possible to monitor continuously the changes in the configuration of the test ankle prosthesis and to collect at any time the data that is characteristic of the positioning of the test intermediate implant 106 relative to the test tibial implant 104.

Preferably, since the measurement means 32 are provided with one or more touch-sensitive members 33, 34, each of which is designed to feel the test ankle prosthesis 101, the reproduction step (c) includes a sub-step (c1) for locking the measurement means 32, during the sub-step the positions of the touch-sensitive members 33, 34 are locked by reversible locking means.

More precisely, with the measurement means 32 comprising a first touch-sensitive member 33 presenting a first feeler surface 33A and a second touch-sensitive member 34 presenting a second feeler surface 34A designed to come into contact respectively with the test tibial implant 104 and with the test intermediate implant 106, the locking sub-step (c1) is performed by fastening the first and second touch-sensitive members to each other.

Most preferably, the practitioner holds the rectangular extension leaves forming touch-sensitive members 33, 34 stationary by compressing them against each other by means of vise-grip pliers when the practitioner considers that the test ankle prosthesis 101 has reached the neutral configuration under the effect of the manipulations performed during the determination step (b). The practitioner can take the configuration measurements and store the collected information durably.

Advantageously, implementing the measurement means 32 does not interfere with the test ankle prosthesis 101, and in particular, does not cause any uncontrolled accidental movement of the block 106, 110 once the neutral configuration is reached.

The reproduction step (c) preferably also includes a fitting sub-step (c2) during which the final ankle prosthesis 1 is configured by means of an assembly template established on the basis of the data collected by the measurement means 32.

More precisely, the fitting sub-step (c2) can comprise a first stage (c'2) subsequent to the locking step (c1), and during which the assembly formed by the touch-sensitive members 33, 34, which are still fastened together, is separated from the test ankle prosthesis 101, and a second stage (c"2) during which the final tibial implant 4 is brought into abutment against the first feeler surface 33A, and the coupling means 10, and more particularly the base 12 thereof, is brought into abutment against the second feeler surface 34A, the touch-sensitive members thereby forming the assembly template for the final ankle prosthesis 1, as shown in FIG. 5.

Advantageously, the final ankle prosthesis 1 can thus be configured on an uncluttered workstation prior to implantation.

Preferably, during the second stage (c"2), the practitioner places the base 12 so that the base 12 is touching the tibial implant 4 at the contact zone 8 and engages the screws 16 without tightening them, and then applies the respective reference surfaces 4A, 12A of the tibial implant and of the base against the touch-sensitive members 33, 34 forming the assembly template so that the touch-sensitive members 33, 34 are put into place spontaneously. Once the base 12 is positioned, the practitioner tightens the screws 16 and then inserts the intermediate implant 6 in the base 12 by engaging the intermediate implant 6 into abutment in the dovetail.

Thus, the practitioner can easily transfer to the final ankle prosthesis 1 a specific configuration that is specific to the patient, and that is determined empirically on the test ankle prosthesis 101 in order to match as well as possible the joint shape of the patient.

Naturally, the present surgical method is in no way limited to implanting an ankle prosthesis.

In particular, the surgical method can constitute a method of implanting a "final prosthesis" in a patient, the method comprising an implantation step (K) for implanting a test prosthesis, during which step a test prosthesis that substantially reproduces the shape of the final prosthesis is implanted in the patient in place of the final prosthesis, a determination step (L) during which a particular operating configuration of the test prosthesis is determined in vivo from among a plurality of possible configurations, and a reproduction step (M) during which the particular operating configuration chosen during the determination step (L) is reproduced on the final prosthesis by means of fitting means with which the final prosthesis is provided.

For purposes of the present invention, the term "operating configuration" is used to mean both the static three-dimensional layout (shapes, volumes, positions, and orientations of the various component elements of the prosthesis) and the arrangements for motion (degrees of freedom) that are implemented during normal operation of the final prosthesis.

For purposes of the invention, the final prosthesis and the test prosthesis can each intrinsically take up a plurality of operating configurations, each operating configuration of the final prosthesis having the counterpart or "homologue" (i.e., in the concept of mathematical sets terminology, the "antecedent") on the test prosthesis. The method of the present invention aims to "adjust" the final prosthesis by previously putting the test prosthesis in situ in order to seek the most suitable operating configuration.

To this end, the test prosthesis of the present invention substantially reproduces the shapes and/or the moving connections of the final prosthesis. The test prosthesis is also designed to be implanted and then replaced with the final prosthesis in a single surgical operation.

The surgical method of the present invention is particularly applicable to putting a joint prosthesis into place in a joint, the prosthesis aims to impart a certain amount of mobility to the joint.

Most preferably, during the determination step (L), a "neutral configuration" is identified empirically as the particular operating configuration of the test prosthesis, in which neutral configuration the stresses exerted on the test prosthesis during the natural movements of the joint are minimized.

Preferably, the determination step (L) comprises a patient manipulation sub-step (L1) during which the patient is placed in a predetermined posture to make it possible to observe the behavior of the test prosthesis under the effect of the manipulation, and an adjustment sub-step (L2) during which the configuration of the test prosthesis is modified as a function of the behavior observed during the manipulation sub-step (L1).

Preferably, the method further comprises a preparation step (O) for preparing the test prosthesis, during which step the test prosthesis is associated with measurement means designed to enable the practitioner to take the measurements of the configuration of the test prosthesis while the test prosthesis is implanted inside the patient.

Thus, particularly advantageously, the prosthesis 1 of the present invention offers an excellent compromise between joint stability, which facilitates the rehabilitation of the patient, in particular in cases of tendon laxity and muscle atrophy, comfort in use, related in particular to the reduced sensation of hindrance, and longevity due to the fact that the prosthesis is subject to only a small amount of wear.

Advantageously, the ankle prosthesis and the methods of the present invention make it possible to personalize the orthopedic treatment for each patient, while also preserving a structure that is simple, and an implementation that is particularly easy and reliable.

The invention claimed is:

1. An ankle prosthesis for use with an ankle, comprising:
   a) a talar implant designed to be implanted in or on the talus;
   b) a tibial implant designed to be implanted in or on the tibia; and
   c) an intermediate implant designed to be interposed between the tibial implant and the talar implant, wherein the intermediate implant is designed to be mounted to move relative to the talar implant at a contact interface in order to allow the ankle to move,
   wherein the ankle prosthesis is provided with configurable coupling means including a base, a first portion of the base being connected to the intermediate implant, said configurable coupling means adapted for adjusting a position of said base relative to the tibial implant angularly about a medullary axis (ZZ') of the tibia and linearly along an axis which is substantially normal to said medullary axis so as to position the base in an angularly and linearly chosen position relative to the tibial implant and for fastening the base to the tibial implant in the chosen position,
   wherein the configurable coupling means include engagement means for engaging the intermediate implant into the tibial implant.

2. The ankle prosthesis of claim 1, wherein the specific configuration of the configurable coupling means is chosen as a function of the particular shape of a joint of the patient in which a patient is to be implanted.

3. The ankle prosthesis of claim 1, wherein the chosen position is referred to as a "neutral configuration" and is chosen such that stresses exerted on the intermediate implant and on the tibial implant during natural movements of the ankle are minimized.

4. The ankle prosthesis of claim 1, wherein a second portion of the base is fastened to the tibial implant and forms a mechanical interface between the tibial implant and the intermediate implant.

5. The ankle prosthesis of claim 4, wherein the base has adjustable fastening means making it possible to choose from among a plurality of possible positions that position in which the second portion of the base is fastened relative to the tibial implant.

6. The ankle prosthesis of claim 5, wherein the adjustable fastening means enable the base to be adjusted continuously.

7. The ankle prosthesis of claim 1, wherein the tibial implant and the base are in a planar abutment relationship, the area of abutment defining a contact zone, so as to make it possible to position the base by using the degrees of freedom offered by the planar abutment relationship of the tibial implant and the base.

8. The ankle prosthesis of claim 7, wherein the contact zone substantially coincides with a plane which is normal to the medullary axis (ZZ') and defined by an axis (XX') of anteroposterior translation and an axis (YY') of mediolateral translation of an ankle joint.

9. The ankle prosthesis of claim 1, wherein the configurable coupling means further comprise fastening means enabling the base to be continuously adjusted among a plurality of possible positions relative to the tibial implant.

10. The ankle prosthesis of claim 1, wherein the intermediate implant has a first contact face and the talar implant has a second contact face, and wherein a contact surface defined by the first and second contact faces is either cylindrically or frustoconically rounded.

11. An ankle prosthesis for use with an ankle, comprising:
    a) a talar implant designed to be implanted in or on the talus;
    b) a tibial implant designed to be implanted in or on the tibia; and
    c) an intermediate implant designed to be interposed between the tibial implant and the talar implant, wherein the intermediate implant is designed to be mounted to move relative to the talar implant at a contact interface in order to allow the ankle to move,
    wherein the ankle prosthesis is provided with configurable coupling means including a base, a first portion of the base being connected to the intermediate implant, said configurable coupling means adapted for adjusting a position of said base relative to the tibial implant angularly about a medullary axis (ZZ') of the tibia and linearly along an axis which is substantially normal to said medullary axis so as to position the base in an angularly and linearly chosen position relative to the tibial implant and for fastening the base to the tibial implant in the chosen position,
    wherein the configurable coupling means include engagement means for engaging the intermediate implant into the tibial implant,
    wherein the chosen position is referred to as a "neutral configuration" and is chosen such that stresses exerted on the intermediate implant and on the tibial implant during natural movements of the ankle are minimized, and
    wherein the neutral configuration corresponds to the intermediate implant in a position relative to the tibial implant firstly wherein the intermediate implant is substantially centered relative to a point of origin about which the movements of the tibia relative to the talus in anteroposterior translation, in mediolateral translation, and in rotation about the medullary axis of the tibia take place, and secondly wherein the tibial implant and the intermediate implant is oriented such that movement axes of the prosthesis substantially coincide with natural anatomical axes of the ankle of the patient.

12. An ankle prosthesis for use with an ankle, comprising:
    a) a talar implant designed to be implanted in or on the talus;
    b) a tibial implant designed to be implanted in or on the tibia; and
    c) an intermediate implant designed to be interposed between the tibial implant and the talar implant, wherein the intermediate implant is designed to be mounted to move relative to the talar implant at a contact interface in order to allow the ankle to move, wherein the ankle prosthesis is provided with configurable coupling means including a base, a first portion of the base being connected to the intermediate implant, said configurable coupling means adapted for adjusting a position of said base relative to the tibial implant angularly about a medullary axis (ZZ') of the tibia and linearly along an axis which is substantially normal to said medullary axis so as to position the base in an angularly and linearly chosen position relative to the tibial implant and for fastening the base to the tibial implant in the chosen position, wherein the base has reception means connecting the intermediate implant to the base, the reception means arranged such that the intermediate implant can occupy a single and predetermined position only relative to the base.

13. An ankle prosthesis for use with an ankle, comprising:
a) a talar implant designed to be implanted in or on the talus;
b) a tibial implant designed to be implanted in or on the tibia; and
c) an intermediate implant designed to be interposed between the tibial implant and the talar implant, wherein the intermediate implant is designed to be mounted to move relative to the talar implant at a contact interface in order to allow the ankle to move,
wherein the ankle prosthesis is provided with configurable coupling means including a base, a first portion of the base being connected to the intermediate implant, said configurable coupling means adapted for adjusting a position of said base relative to the tibial implant angularly about a medullary axis (ZZ') of the tibia and linearly along an axis which is substantially normal to said medullary axis so as to position the base in an angularly and linearly chosen position relative to the tibial implant and for fastening the base to the tibial implant in the chosen position,
the ankle prosthesis further comprising reference means indicating an arrangement of the intermediate implant relative to the tibial implant in order to enable the practitioner to configure the configurable coupling means accurately.

14. The ankle prosthesis of claim 13, wherein the reference means have a first reference surface associated with the tibial implant and a second reference surface associated with the base, the relative position of the first and second reference surfaces determine a position of the base in a frame of reference formed by the tibial implant.

15. An ankle prosthesis for use with an ankle, comprising:
a) a talar implant designed to be implanted in or on the talus;
b) a tibial implant designed to be implanted in or on the tibia; and
c) an intermediate implant designed to be interposed between the tibial implant and the talar implant, wherein the intermediate implant is designed to be mounted to move relative to the talar implant at a contact interface in order to allow the ankle to move,
wherein the ankle prosthesis is provided with configurable coupling means including a base, a first portion of the base being connected to the intermediate implant, said configurable coupling means adapted for adjusting a position of said base relative to the tibial implant angularly about a medullary axis (ZZ') of the tibia and linearly along an axis which is substantially normal to said medullary axis so as to position the base in an angularly and linearly chosen position relative to the tibial implant and for fastening the base to the tibial implant in the chosen position,
wherein the configurable coupling means comprises a plurality of broad-headed screws, each screw having a shank, each screw shank slidingly cooperating with one or more grooves provided in the base, so as to make it possible to couple the base loosely to the tibial implant, and then to adjust the position of the base linearly or angularly relative to the tibial implant and finally to tighten the screw so as to hold the base stationary against the tibial implant.

16. An ankle prosthesis for use with an ankle, comprising:
a) a talar implant designed to be implanted either in or on the talus;
b) a tibial implant designed to be implanted either in or on the tibia;
c) an intermediate implant interposed between the tibial implant and the talar implant, wherein the intermediate implant is mounted to move relative to the talar implant at a contact interface in order to allow the ankle to move;
d) a configurable coupling comprising
  i) a base associated with the intermediate implant,
  ii) an engaging element for engaging the base to the tibial implant and for adjusting the position of said base relative to the tibial implant angularly about a medullary axis (ZZ') of the tibia and linearly along an axis which is substantially normal to said medullary axis so as to position the base in an angularly and linearly selected position relative to the tibial implant, and
  iii) a fastener for fastening the base to the tibial implant in the selected position,
wherein the base further comprises a receptacle connecting the intermediate implant to the base, the receptacle being arranged such that the intermediate implant can occupy a single and predetermined position only relative to the base.

17. An ankle prosthesis for use with an ankle, comprising:
a) a talar implant designed to be implanted either in or on the talus;
b) a tibial implant designed to be implanted either in or on the tibia;
c) an intermediate implant interposed between the tibial implant and the talar implant, wherein the intermediate implant is mounted to move relative to the talar implant at a contact interface in order to allow the ankle to move;
d) a configurable coupling comprising
  i) a base associated with the intermediate implant,
  ii) an engaging element for engaging the base to the tibial implant and for adjusting the position of said base relative to the tibial implant angularly about a medullary axis (ZZ') of the tibia and linearly along an axis which is substantially normal to said medullary axis so as to position the base in an angularly and linearly selected position relative to the tibial implant, and
  iii) a fastener for fastening the base to the tibial implant in the selected position,
further including a reference indicator comprising a first reference surface associated with the tibial implant and a second reference surface associated with the base, a relative position of the first and second reference surfaces determine the position of the base in a frame of reference formed by the tibial implant.

18. An ankle prosthesis for use with an ankle, comprising:
a) a talar implant designed to be implanted in or on the talus;
b) a tibial implant designed to be implanted in or on the tibia; and
c) an intermediate implant designed to be interposed between the tibial implant and the talar implant, wherein the intermediate implant is designed to be mounted to move relative to the talar implant at a contact interface in order to allow the ankle to move,
wherein the ankle prosthesis is provided with configurable coupling means including a base, a portion of the base being connected to the intermediate implant, said configurable coupling means for adjusting a position of said base relative to the tibial implant angularly about a medullary axis (ZZ') of the tibia and linearly along an axis which is substantially normal to said medullary axis so as to position the base in an angularly and linearly chosen position relative to the tibial implant and for restraining movement of the base to the tibial implant in the chosen position.

* * * * *